(12) United States Patent
Casse et al.

(10) Patent No.: US 10,971,266 B2
(45) Date of Patent: Apr. 6, 2021

(54) TRANSFER OF BREATHING ASSISTANCE APPARATUS DATA

(71) Applicant: Fisher & Paykel Healthcare Limited, Auckland (NZ)

(72) Inventors: Benjamin Wilson Casse, Auckland (NZ); Matthew Joel Read, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1102 days.

(21) Appl. No.: 14/646,675

(22) PCT Filed: Nov. 21, 2013

(86) PCT No.: PCT/IB2013/060290
§ 371 (c)(1),
(2) Date: May 21, 2015

(87) PCT Pub. No.: WO2014/080351
PCT Pub. Date: May 30, 2014

(65) Prior Publication Data
US 2015/0302159 A1    Oct. 22, 2015

Related U.S. Application Data

(60) Provisional application No. 61/729,744, filed on Nov. 26, 2012.

(51) Int. Cl.
*G16H 40/63*       (2018.01)
*G16H 10/60*       (2018.01)
(Continued)

(52) U.S. Cl.
CPC ......... *G16H 40/63* (2018.01); *G06F 16/9554* (2019.01); *G16H 10/60* (2018.01);
(Continued)

(58) Field of Classification Search
CPC .......... G06F 19/3406; G06F 17/30879; G16H 40/20; G16H 10/60; H04L 41/0293; H04L 67/12; F04C 2270/041
(Continued)

(56) References Cited

U.S. PATENT DOCUMENTS 6,993,573 B2 *  1/2006  Hunter ................ G06F 16/9554
                                                    709/218
8,341,516 B1 * 12/2012  Mason .................... G06F 40/14
                                                    715/238
(Continued)

FOREIGN PATENT DOCUMENTS

CN       104520855          4/2015
DE    102013205591 A1 *    10/2014   ............. H04L 51/28
(Continued)

OTHER PUBLICATIONS

Berners-Lee, T., Masinter, L., and McCahill, M., Uniform Resource Locators (URL), University of Minnesota, Dec. 1994, p. 15 (Year: 1994).*

(Continued)

*Primary Examiner* — Robert A Sorey
*Assistant Examiner* — Kimberly A. Sass
(74) *Attorney, Agent, or Firm* — Knobbe, Martens, Olson & bear, LLP

(57) ABSTRACT

A medical apparatus is adapted to facilitate a transfer of data to a computer system using a mobile device. The apparatus has a store of data, a display and a controller that generates a barcode encoding an access address for the computer system and the data, and displaying the barcode on the display.

24 Claims, 7 Drawing Sheets

(51) Int. Cl.
*G16H 40/20* (2018.01)
*G06F 16/955* (2019.01)
*H04L 12/24* (2006.01)
*H04L 29/08* (2006.01)

(52) U.S. Cl.
CPC ......... *G16H 40/20* (2018.01); *H04L 41/0293* (2013.01); *H04L 67/12* (2013.01); *F04C 2270/041* (2013.01)

(58) Field of Classification Search
USPC .............................................................. 705/2
See application file for complete search history.

(56) References Cited

U.S. PATENT DOCUMENTS

| | | | |
|---|---|---|---|
| 9,092,705 | B2 | 7/2015 | Zhuang |
| 9,177,109 | B2* | 11/2015 | Steinhauer .......... G06F 19/3418 |
| 2007/0145137 | A1* | 6/2007 | Mrowiec .................. A61B 5/00 |
| | | | 235/462.01 |
| 2007/0233521 | A1* | 10/2007 | Wehba .................. A61M 5/142 |
| | | | 705/3 |
| 2008/0149701 | A1* | 6/2008 | Lane ................ G06K 19/06028 |
| | | | 235/375 |
| 2008/0164305 | A1 | 7/2008 | Ball |
| 2009/0069000 | A1 | 3/2009 | Kindberg et al. |
| 2012/0067944 | A1* | 3/2012 | Ross .................... G06K 7/1095 |
| | | | 235/375 |

FOREIGN PATENT DOCUMENTS

| | | |
|---|---|---|
| GB | 2408614 A | 6/2005 |
| GB | 2446211 B | 6/2008 |
| WO | WO 2002/015121 A1 | 2/2002 |
| WO | WO 2005/001628 | 1/2005 |
| WO | WO 2008/079771 A1 | 7/2008 |
| WO | WO 2008/094645 A2 | 8/2008 |
| WO | WO 2012/040486 A2 | 3/2012 |
| WO | WO 2012/120078 | 9/2012 |

OTHER PUBLICATIONS

International Search Report; PCT/IB2013/060290; dated Mar. 31, 2014.
Written Opinion of the ISA; PCT/IB2013/060290; dated Mar. 31, 2014.
Chinese Office Action; dated Apr. 5, 2017; 18 pages.
Chinese Office Action; dated Dec. 14, 2017; 30 pages.
European Office Action; dated Jul. 25, 2017; 6 pages.
Extended European Search for Application No. 20156130.5 dated Jun. 5, 2020; 8 pages.

* cited by examiner

TRANSFER OF BREATHING ASSISTANCE APPARATUS DATA

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

1. Field of the Invention

The present invention relates to transferring data obtained by a medical apparatus (such as a breathing assistance apparatus like a CPAP machine or similar) to a computing system for storage and/or subsequent processing and/or review.

2. Description of the Related Art

Patients use medical apparatus to help with treatment of their ailments. Medical data relating to patients and/or their use of the medical apparatus is frequently captured and stored for the purposes of monitoring patients' health and assisting with their healthcare, or for monitoring the apparatus itself to ensure it is operating properly. Often, such data is captured by the medical apparatus that the patient is using, or that is otherwise being operated to monitor or assist the patient.

An example of such a medical apparatus is a breathing assistance apparatus. Breathing assistance apparatus are used for a variety of purposes, including PAP, flow and/or oxygen treatment and the like. When using such apparatus to treat a condition, it is important that the patient complies with the treatment prescription provided by their healthcare professional. If they do not comply with the treatment prescription (such as not using the apparatus in accordance with the healthcare professionals direction) then the treatment may not be successful. Compliance of the patient to their prescription is of interest to insurance providers who fund the apparatus and treatment, and also the dealers who provide the apparatus to patients. Breathing apparatus can record compliance data for analysis so that patient compliance can be monitored and actions taken if necessary. The compliance data is normally obtained from sensors and other processors in the apparatus itself. Other information can also be captured more generally relating to medical apparatus usage and also therapy and physiology of the patient, or to operation of the medical apparatus itself (such as diagnostics information).

Various interested parties may wish to access that information. Those parties can be for example, one or more of a patient, healthcare professional, dealer, insurance provider, manufacturer or other interested party.

SUMMARY OF THE INVENTION

It is an object of the present invention to provide a method, system, software and/or apparatus for transferring data from a medical apparatus to a computer system.

In one aspect the present invention may be said to consist in a method of transferring data from a medical apparatus to a computer system comprising generating a barcode that encodes an access address for the computer system and the data, and displaying the barcode on a display of the medical apparatus.

Preferably the barcode is one of a: 2D barcode, 1D barcode. Preferably the barcode is dynamically generated each time data is generated and/or needs to be transferred.

Preferably the data is or comprises patient data.

Preferably the patient data comprises: runtime (in hours from 0.0 to 10.0); usage time (in hours from 0.0 to 10.0); AHI (in index up to 255); leak (in litres per minute up to 120); compliance data; usage data; and efficacy data.

Preferably the data is or comprises medical apparatus data.

Preferably the medical apparatus data comprises diagnostics data.

Preferably the medical device is a breathing assistance apparatus, such as a PAP apparatus; a flow therapy apparatus; or similar Preferably the access address is one of: IP address; URL; website address; and network address.

Preferably the barcode encodes a URL comprising the access address and the data as a sub path appended to the access address.

Preferably the method further comprises: capturing an image of the barcode from the display; and accessing the computer system using the URL including transferring the URL with data as a sub path appended to the URL.

Preferably the method further comprises: receiving the URL; extracting the sub path; storing the data; and optionally returning the data for review Preferably returning the data for review comprises generating code from the data in the sub path that can be transferred to and used by a computing device for display of the data.

In another aspect the present invention may be said to consist in a method of providing data for review and/or storage comprising: receiving a URL comprising an access address and data as a sub path appended to the access address, extracting the sub path, storing the data optionally returning the data for review.

Preferably returning the data for review comprises generating code from the data in the sub path that can be transferred to and used by a computing device for display of the data.

In another aspect the present invention may be said to consist in a method of transferring data from a medical apparatus to a computer system comprising using a mobile device to: capture on a mobile device an image of a barcode displayed on the medical apparatus that encodes an access address for the computer system and the data, access the computer system using the access address in the barcode, transfer the data in the barcode to the computer system.

Preferably the barcode is one of a: 2D barcode, 1D barcode. Preferably the method further comprises receiving code generated by the computer system from the data in the sub path and using the code to display the data of the mobile device.

In another aspect the present invention may be said to consist in a method for transferring data comprising encoding medical apparatus data into a URL also comprising an access address for a destination computer system, the method preferably further comprising generating a barcode encoding the URL.

In another aspect the present invention may be said to consist in a computer system for storing data from a medical apparatus comprising: receiving from a mobile device an access request at an access address defined in a URL obtained by the mobile device from a barcode display on a medical apparatus, the access request comprising the access address and data appended as a sub path to the URL, the URL being encoded in the barcode, storing the data, optionally returning the data for review Preferably returning the data for review comprises generating code from the data in the sub path that can be transferred to and used by a computing device for display of the data.

In another aspect the present invention may be said to consist in a medical apparatus adapted to facilitate transfer of data to a computer system using a mobile device comprising: a store of data, a display, and a controller that generates a barcode encoding an access address for the computer system and the data, and displaying the barcode on the display.

Preferably the controller dynamically generates the barcode each time data is generated and/or needs to be transferred.

Preferably the data is or comprises patient data.

Preferably the patient data comprises:runtime (in hours from 0.0 to 10.0); usage time (in hours from 0.0 to 10.0); AHI (in index up to 255); leak (in litres per minute up to 120); compliance data; usage data; and efficacy data Preferably the data is or comprises medical apparatus data.

Preferably the medical apparatus data comprises diagnostics data.

Preferably the medical device is a breathing assistance apparatus, such as PAP apparatus; flow therapy apparatus; or similar.

Preferably the access address is at least one of: IP address; URL; a website address; and network address.

Preferably the barcode encodes a URL comprising the access address and the data as a sub path appended to the access address.

The data (also termed "medical data"), can be patient data and/or medical apparatus data. Patient data can comprise, for example, data about the patient (e.g. physiological data) and/or data about the patient's use of the medical apparatus (such as compliance data, usage date, efficacy data or the like). Medical apparatus data can comprise, for example, diagnostics or other data relating to operation of the medical device. There can be overlap between the different types of data and the explanation and categorisation above should not be considered limiting.

In this specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth. The invention consists in the foregoing and also envisages constructions of which the following gives examples only.

BRIEF DESCRIPTION OF THE DRAWINGS

Preferred embodiments of the invention will now be described with reference to the following figures, of which:

FIGS. 4A and 4B show display of data received from a computer system displayed on an application or browser on a mobile device, computer or similar.

DETAILED DESCRIPTION OF THE PREFERRED EMBODIMENT

Figure 1:
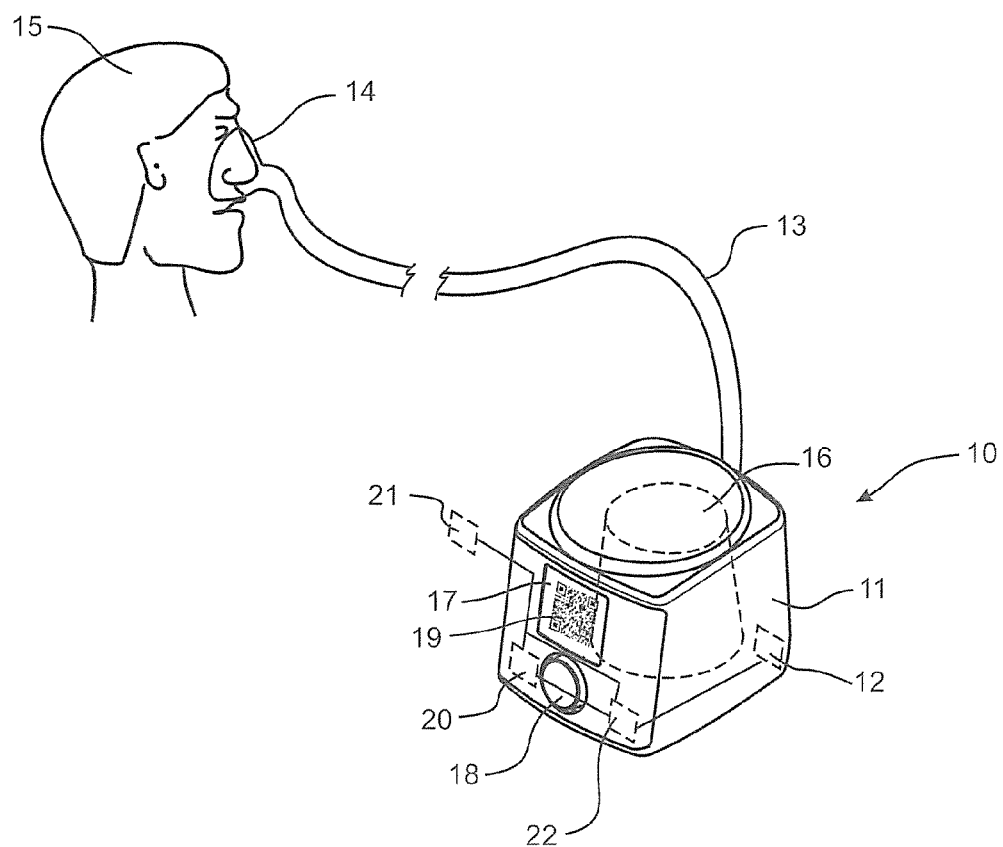
FIG. 1 shows medical apparatus displaying a two-dimensional barcode that encodes data from a medical apparatus.

FIG. 1 shows in schematic form a breathing assistance apparatus 10, such as a CPAP apparatus, configured to display a two-dimensional barcode 19 encoding data (medical data) collected by the apparatus 10 in accordance with the present invention for subsequent transfer, storage and/or review. It will be appreciated that while the present invention is described in relation to a CPAP apparatus, this should not be considered limiting and the invention can be utilised in relation to any medical apparatus that captures data relating to a patient and/or operation of the apparatus, such as apparatus use, apparatus operating parameters and diagnostics, patient physiological or health parameters or the like. All such information (including patient and apparatus information) can be generally termed "medical data".

The CPAP apparatus 10 can be known to those skilled in the art and comprises a housing 11 with an internal blower 12 (shown in dotted schematic form) for providing pressurised air to a patient 15 via a conduit 13 and a patient interface 14. An internal/external or separate interconnectable chamber 16 (shown dotted as internal chamber in FIG. 1) can be used to humidify the pressurised air. The CPAP apparatus 10 comprises a user interface 17, 18, which itself comprises a display 17 and other output interface as required, and also user input interface with devices such as buttons, switches, dials 18 and the like. The CPAP apparatus 10 also comprises a number of sensors 20, 21, including flow, pressure, temperature, humidity and other sensors internal to or otherwise forming part of the medical apparatus (see generally 20) and possibly comprises or can be connected to external sensors (see, e.g. 21) that measure physiological parameters of the patient, such as heart rate, breathing rate, temperature, humidity, pressure, flow and the like.

The apparatus can be controlled by a controller 22, such as a microprocessor, microcontroller or similar, that receives input via the user input interface 18, operates the apparatus and is configured to provide output on the user output 17, including the display. The controller can have internal memory and/or also access external memory. The controller can also receive input from the sensors 20, 21 and record, process, store and collate the information for transfer, storing, reporting and review purposes by a physician, patient, medical device dealer, insurance company, manufacturer or other interested party. Among other things, the controller 22 is configured via a program or otherwise to take the captured information and encode it into the two-dimensional barcode 19 for display on the medical apparatus display 17. The two-dimensional (2D) barcode 17 encodes a) the access address of a computer system (such as the IP address/URL/website address of a website running on a webserver) to which the data is to be transferred, and b) appended data that represents the (medical) data captured by the controller from the medical apparatus. The two dimensional barcode 19 is used to assist transfer of the medical data on the apparatus 10 to a computer system 30 (see FIG. 3) for storage, processing and distribution for review/display.

Figure 1A:
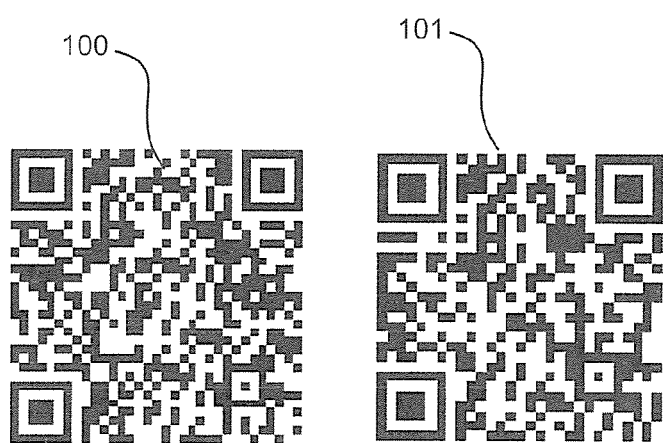
FIG. 1A shows two examples of possible two-dimensional codes that might be displayed on the medical apparatus.

Two-dimensional barcodes and their generation are known to those skilled in the art and any suitable process could be used for encoding of the data into a two-dimensional barcode. The two-dimensional barcode can take any form known to those skilled in the art and can be generated using any suitable algorithm or other process. One such example of a two-dimensional barcode is a QR code, but this is not the only option. Generic examples of two-dimensional barcodes 100, 101 are shown in FIG. 1A. Also, the invention could utilise instead of a two-dimensional barcode, any other type of ID or scannable image with encoded data and access address. For example, a 1D barcode could be used. The present description refers to a two-dimensional barcode but this should not be considered limiting and any reference/description to a two-dimensional barcode could also be applied to a one-dimensional (1D) barcode instead. The use and encoding of one-dimensional barcodes is know those skilled in the art and upon regadin this specification any application to two-dimensional barcodes of the invention could be readily adapted to one-dimensional barcodes by those skilled in the art.

Figure 2:
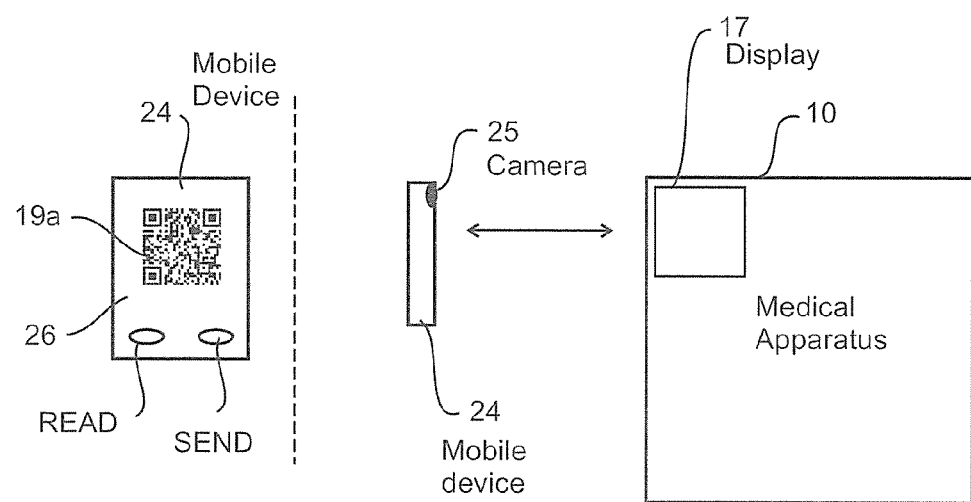
FIG. 2 shows a mobile device executing software for reading and transferring data in accordance with the two-dimensional barcode displayed on the medical apparatus.

Referring to FIG. 2, to transfer the medical data from the medical apparatus to the computer system 30, a mobile device 24 is used (such as a PDA or mobile telecommunications device such as a smartphone). It comprises a camera 25 and also executes suitable barcode reader software/application 26 (known to those skilled in the art) which is used to capture an image 19a of the two-dimensional barcode 19 on the display of the medical apparatus 10, and process the barcode 19 for subsequent transfer of the encoded medical data to a computer system with the encoded access address. To achieve this, the camera 25 of the mobile device 24 is held close to the display 17 of the medical apparatus to take a photograph of the two-dimensional barcode 19, and the reader application facilitates the required processing and telecommunications functions (in conjunction with mobile device hardware) to access and transfer data to the computer system 30. Mobile devices 24, their hardware and functionality, and reader applications will be known to those skilled in the art.

Figure 3:
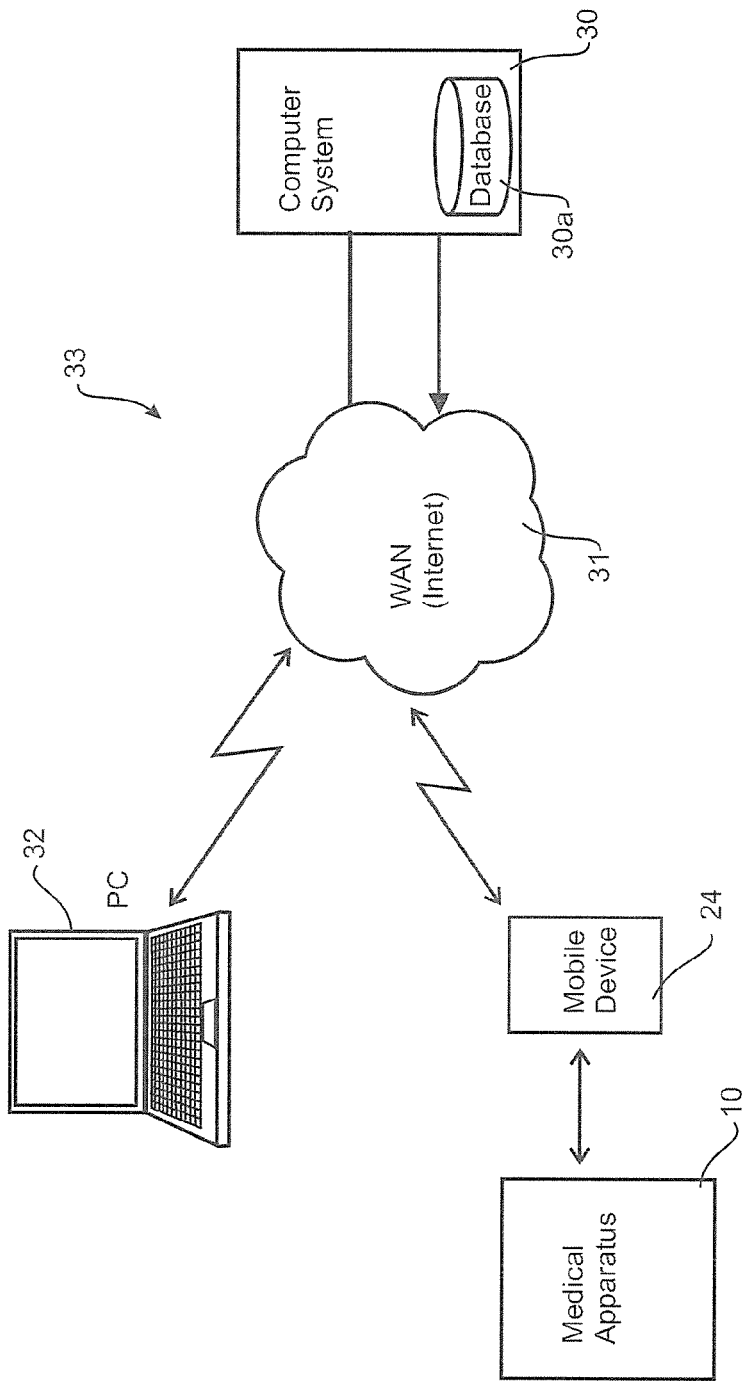
FIG. 3 shows a system for transferring data to a computer system for subsequent storage, processing and/or review.

FIG. 3 shows a typical system 33 that enables capture, transfer, storage and review/display of medical data from a medical apparatus utilising a two-dimensional barcode. The system comprises the medical apparatus 10 of FIG. 1 and the mobile device 24 of FIG. 2. The mobile device 24, once it has captured the two-dimensional barcode, uses the information encoded therein to access the computer system 30/database 30a and transfer the medical apparatus data. Typically, the mobile device 24 accesses the computer system via the internet or other wide-area network 31, using an IP address or URL (comprising a website address) or other suitable network address (access address) encoded in the two-dimensional barcode. It accesses the wide area network through a GPRS or GSM network or via any other suitable mode (either directly or indirectly, wired or wireless).

Typically, the computer system 30 will be or run a web server, and the access address will be a website address of a website running on that that web server. Typically the barcode will encode a URL, which itself comprises the website address, plus has the medical apparatus data appended to the website address as a sub path. Once the web server has been accessed, the medical apparatus data appended to the computer system address is transferred to the computer system. Typically, where a URL is utilised, the entire URL will be submitted and the webserver will extract from it the medical apparatus data in the appended sub path. The invention is not just restricted to barcodes encoding URLs, web addresses and webservers, and this example should be seen as illustrative only. Once extracted, the medical data is processed, stored (in database 30a), collated and then sent back via the wide area network 31 to the mobile device 24 for review on an app, browser or similar software viewer. Alternatively, the information could be sent back and accessed by a mobile device of another interested party, or the personal computer 32 of an interested via a browser or similar. The information can be viewed via such modes by any interested party.

Figure 4A:
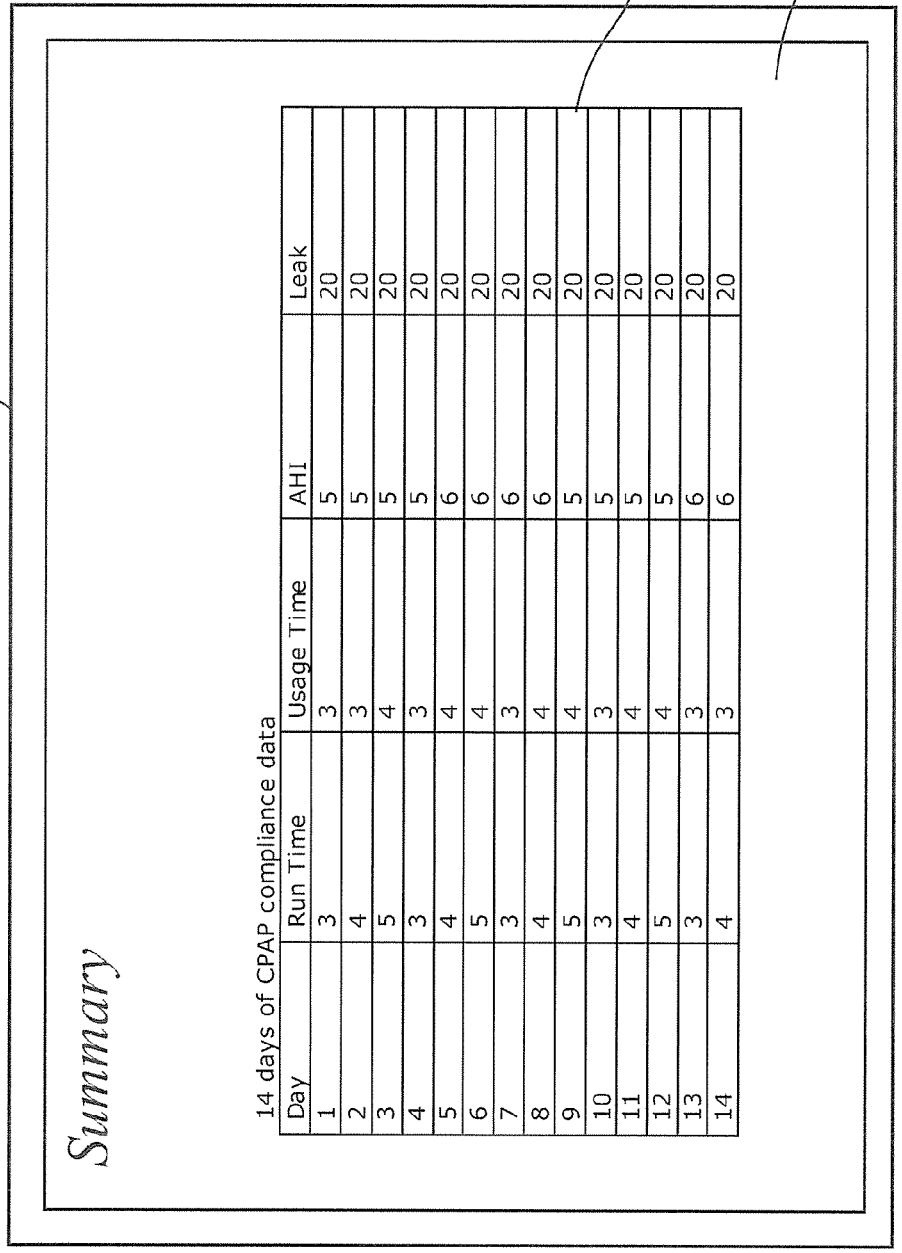
Figure 4B:
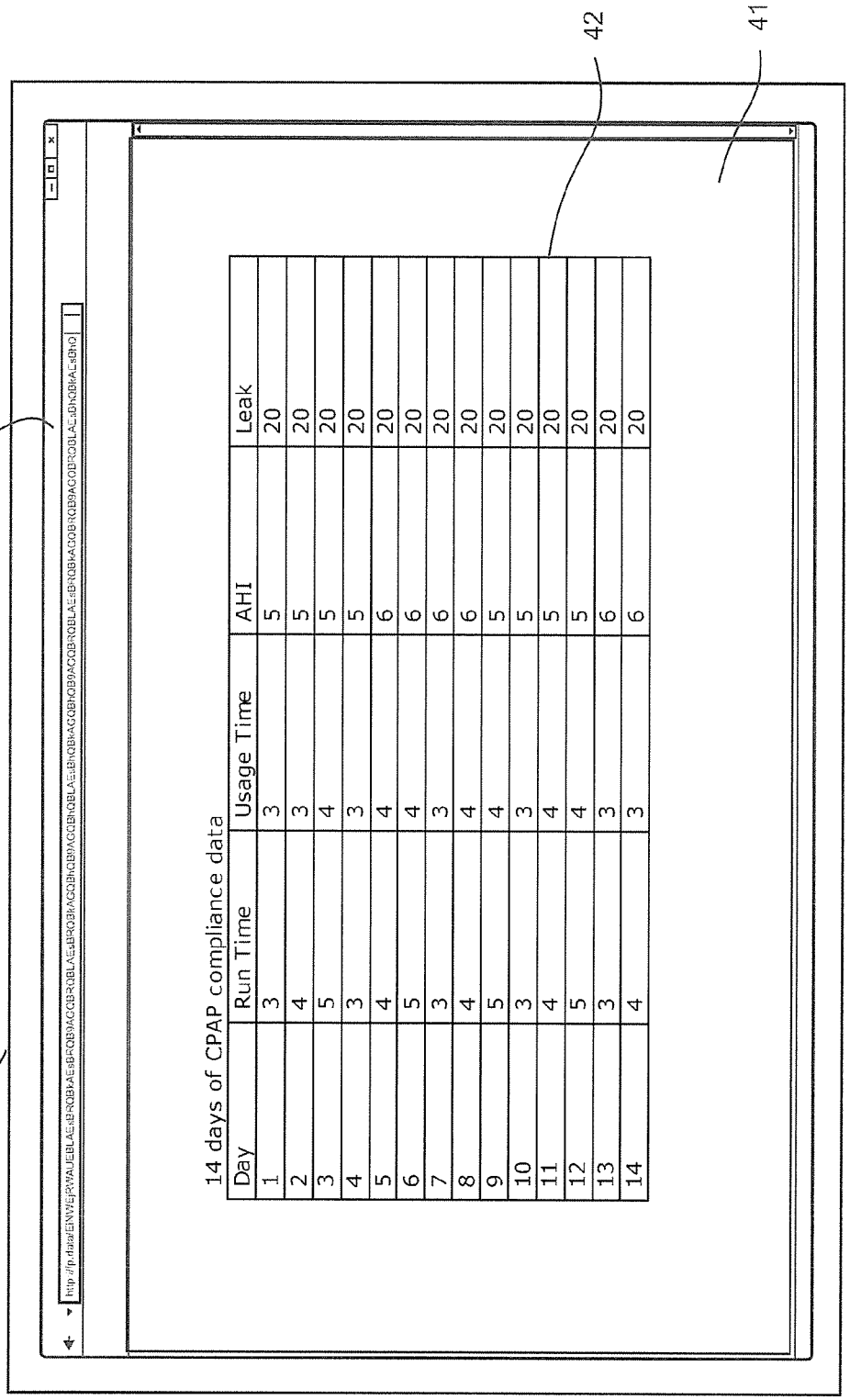

FIG. 4A shows (generic) data from a medical apparatus received from the computer system 30 being displayed on an application (e.g. app) 40 running on the mobile device 24 or personal computer 32 or other computing device. FIG. 4B shows display of the same information, but in a browser either running on a mobile device or a personal computer or other computing device. The access address and medical apparatus data encoded in the two-dimensional barcode (in this case in the form of a URL) is also displayed.

Figure 5:
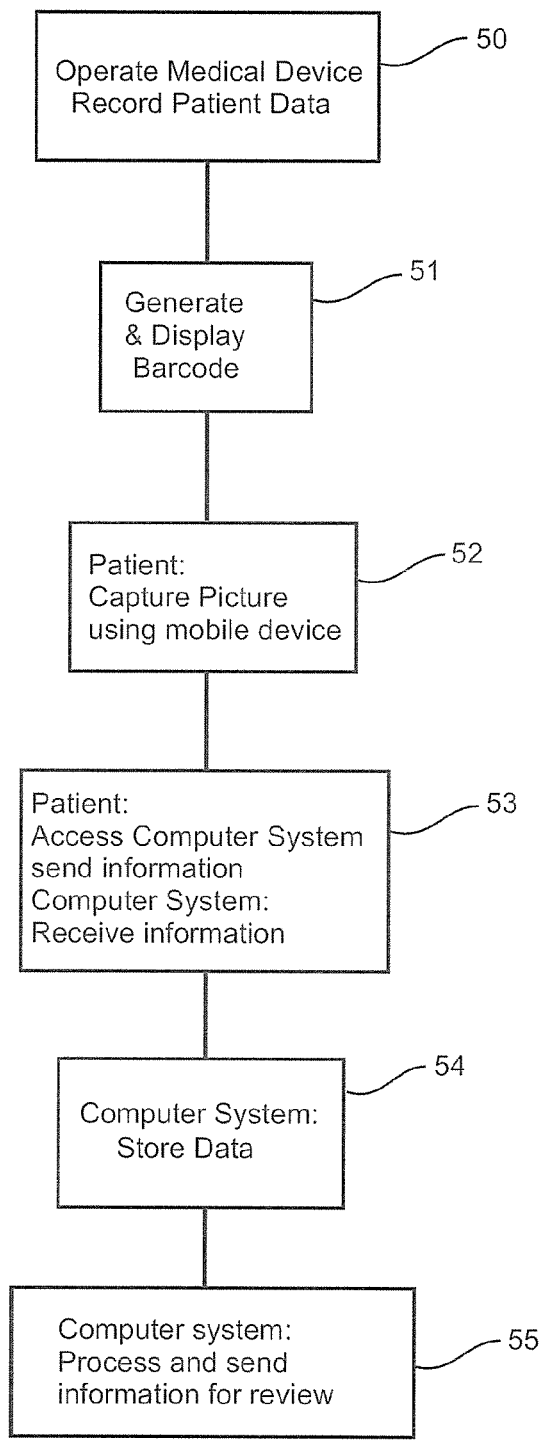
FIG. 5 shows a flow diagram of use and operation of the invention.

General operation of the invention will now be described with reference to FIG. 5. A CPAP apparatus or other medical apparatus 10 is operated in the usual manner, collecting data from its sensors 20, 21 and other internal inputs on the operation of the apparatus and also physiological parameters of the patient, step 50. These are stored in memory (for example in internal or external memory access by the controller 12) in the medical apparatus in the usual manner. As and when required, the controller 12 is manually prompted or automatically triggered to generate a two-dimensional barcode 19 that encodes the access address of the computer system 30 that is to process and distribute the information for review, and encodes the medical data. The two-dimensional barcode 19 is then displayed on the display 17 of the medical apparatus 10 by the controller 12, step 51. This again could be triggered automatically, or by a user operating the user interface 18 of the apparatus 10. The patient or other user then operates their mobile device 24 to capture an image 19a of the two-dimensional barcode 19, step 52, and uses it to access and transfer the medical data to a computer system 30, step 53. They do this by activating a reader application on the mobile device 24, using the application to take a picture 19a of the two-dimensional barcode 19 displayed on the medical apparatus by holding the camera 35 up to the medical apparatus display 17. The user then operates the reader application to access the computer system 30 from their mobile device 24 over the wide area network 31, step 53. The reader application decodes the barcode to extract the URL comprising the access address and sub path with medical data. The read application then contacts the webserver identified by the URL in the usual way—e.g. by contacting ISPs/DNSs to resolve the IP address of the webserver linked to the access address in the URL. The reader then sends an HTTP get request to the webserver associated with the URL. The webserver receives the URL and passes the encoded medical data (in the sub path of the URL) to a service that dynamically generates HTML (from the encoded medical data) for rendering a webpage that displays the medical data in a suitable format on a reader app/browser. The computer system 30 then stores the data in the database 30a, step 54, processes the data where necessary and transfers the HTML page (comprising a summary of the patient data) back to the mobile device or other computing device where it is rendered for display by an application/browser on the device for review, step 55. Alternatively, it could be reviewed in another application, browser or similar either on the mobile device or on another computing device such as a personal computer that can access the computer system via the access address. Alternatively, other type of data could be transferred back to the mobile device or other computing device, such as XML or raw data. Alternatively, the computer system 30 does not transfer data back to the mobile device or other computer device, but rather simply stores, processes and/or uses the data.

The operation of the invention will now be described in more detail with reference to a particular example. This example should not be considered limiting, and is provided for illustrative purposes only.

A CPAP apparatus 10 has the Ser. No. 12/345,6123456. A computer system 30 for transferring the captured data to has the URL (access address) http://fp.data/

During operation of a CPAP apparatus 10 over a period of 14 days, some or more of the following medical data (in this case patient data) is recorded by the controller 12 from the sensors 20, 21 and internal inputs: device serial number (12 digits); 14 days of the following: runtime (in hours from 0.0 to 10.0); usage time (in hours from 0.0 to 10.0); AHI (in index up to 255); and leak (in litres per minute up to 120).

The data is stored in any suitable medium (such as memory internal or external to the controller 12) using any suitable format. An example of patient data that could be recorded and stored in the apparatus 10 is represented below in a table format.

TABLE 1

14 days of CPAP compliance data

| Day | Run Time | Usage Time | AHI | Leak |
|---|---|---|---|---|
| 1 | 3 | 3 | 5 | 20 |
| 2 | 4 | 3 | 5 | 20 |
| 3 | 5 | 4 | 5 | 20 |
| 4 | 3 | 3 | 5 | 20 |
| 5 | 4 | 4 | 6 | 20 |
| 6 | 5 | 4 | 6 | 20 |
| 7 | 3 | 3 | 6 | 20 |
| 8 | 4 | 4 | 6 | 20 |
| 9 | 5 | 4 | 5 | 20 |
| 10 | 3 | 3 | 5 | 20 |
| 11 | 4 | 4 | 5 | 20 |
| 12 | 5 | 4 | 5 | 20 |
| 13 | 3 | 3 | 6 | 20 |
| 14 | 4 | 3 | 6 | 20 |

TABLE 1-continued

Next, the controller 12 generates the two-dimensional barcode 19 for this data. The controller does this at any suitable time, generally after data has been recorded for the required period of time and transfer is desired. The information is encoded into a barcode using any suitable process. In this case, a URL containing the upload web (access) address and the medical data is generated and encoded into the barcode. To do this, the medical apparatus data is encoded into a byte array in the format:

6 bytes [serial number]|2 bytes [Period Start]|(day 1 data)|byte [Runtime×10], 1 byte [Usage×10], 1 byte [AHI], 1 byte [leak]|(day 2 data) . . . .

So that:

Serial Number (6 Bytes BCD): 0x12, 0x23, 0x56, 0x12, 0x34, 0x56

Period Start Date (MSDOS Date Format): 0x01, 0x41 resulting in the encoded data shown in the table below:

TABLE 2

Encoded Data

| Day | Run Time | Usage Time | AHI | Leak |
|---|---|---|---|---|
| 1 | 0 × 01 0 × 2C | 0 × 01 0 × 2C | 0 × 05 | 0 × 14 |
| 2 | 0 × 01 0 × 90 | 0 × 01 0 × 2C | 0 × 05 | 0 × 14 |
| 3 | 0 × 01 0 × F4 | 0 × 01 0 × 90 | 0 × 05 | 0 × 14 |
| 4 | 0 × 01 0 × 2C | 0 × 01 0 × 2C | 0 × 05 | 0 × 14 |
| 5 | 0 × 01 0 × 90 | 0 × 01 0 × 90 | 0 × 06 | 0 × 14 |
| 6 | 0 × 01 0 × F4 | 0 × 01 0 × 90 | 0 × 06 | 0 × 14 |
| 7 | 0 × 01 0 × 2C | 0 × 01 0 × 2C | 0 × 06 | 0 × 14 |
| 8 | 0 × 01 0 × 90 | 0 × 01 0 × 90 | 0 × 06 | 0 × 14 |
| 9 | 0 × 01 0 × F4 | 0 × 01 0 × 90 | 0 × 05 | 0 × 14 |
| 10 | 0 × 01 0 × 2C | 0 × 01 0 × 2C | 0 × 05 | 0 × 14 |
| 11 | 0 × 01 0 × 90 | 0 × 01 0 × 90 | 0 × 05 | 0 × 14 |
| 12 | 0 × 01 0 × F4 | 0 × 01 0 × 90 | 0 × 05 | 0 × 14 |
| 13 | 0 × 01 0 × 2C | 0 × 01 0 × 2C | 0 × 06 | 0 × 14 |
| 14 | 0 × 01 0 × 90 | 0 × 01 0 × 2C | 0 × 06 | 0 × 14 |

Resulting in a binary blob representing this data of: 0x12, 0x23, 0x56, 0x12, 0x34, 0x56, 0x01, 0x41, 0x01, 0x2C, 0x01, 0x2C, 0x05, 0x14, 0x01, 0x90, 0x01 0x2C, 0x05, 0x14, 0x01, 0xF4, 0x01, 0x90, 0x05, 0x14, 0x01, 0x2C, 0x01k 0x2C, 0x05, 0x14, 0x01, 0x90, 0x01, 0x90, 0x06, 0x14, 0x01, 0xF4, 0x01, 0x90, 0x06, 0x14, 0x01, 0x2C, 0x01, 0x2C, 0x06, 0x14, 0x01, 0x90, 0x01, 0x90, 0x06, 0x14, 0x01, 0xF4, 0x01, 0x90, 0x05, 0x14, 0x01, 0x2C, 0x01, 0x2C, 0x05, 0x14, 0x01, 0x90, 0x01, 0x90, 0x05, 0x14, 0x01, 0xF4, 0x01, 0x90, 0x05, 0x14, 0x01, 0x2C, 0x01, 0x2C, 0x06, 0x14, 0x01, 0x90, 0x01, 0x2C, 0x06, 0x14

The binary array then base 64 encoded to get a text (e.g. ascii) representation as following: EiNWEjRWAUEB LAEsBRQBkAEsBRQB9AGQBRQBLAEsBRQBkAGQB hQB9AGQBhQBLAEsB hQBkAGQBhQB9AGQBRQ BLAEsBRQBkAGQBRQB9AGQBRQBLAEsBhQBkAEs BhQ=

This encoded string is appended to the website (access) address http:fp.data/ to create a URL as follows with the above string as an appended sub path: http://fp.data/ EiNWEjRWAUEBLAEsBRQBkAEsBRQB9AGQBRQBL AEsBRQBkAGQBhQB9AGQBhQBLAEsBhQBkA GQBh QB9AGQBRQBLAEsBRQBkAGQBRQB9AGQBRQBLA EsBhQBkA EsBhQ=

Figure 6:
FIG. 6 shows a two-dimensional barcode in accordance with one example.

By using the standard QR code encoding of a URL, the QR code (shown in FIG. 6) is obtained which embodies the URL.

A URL is a standard piece of data supported by the QR specification. When a QR reader scans a QR code containing a URL by definition the reader application will attempt to access the URL (which comprises the access address and the data) as encoded in the QR code. The URL is accessed with a standard HTTP request, where the first part of the URL (before the "/") is used to locate the destination server and the content after the "/" is submitted to the remote server and generally used to reference a path on the remote server containing content to return to the client. This implementation overrides how this content after the "/" is processed by the server in that rather than using it to reference a path containing content, the server contains a pre-processor that intercepts the request and extracts the data. Extracting the data involves performing the steps required to encode the data in reverse order. The information is then stored in a database indexed by device serial number. Once the data has been stored the pre-processor dynamically composes an HTML web page consisting of the device identifier and line graphs showing the trends of each of the data fields (runtime, usage time, AHI, Leak) over the 14 days of data submitted. This HTML content is then returned to the client as if it was a static page that had been referenced by the URL path. As far as the client is concerned it has accessed a static HTML page. Alternatively, other types of data could be transferred back to the mobile device or other computing device, such as XML or raw data. Alternatively, the computer system 30 does not transfer data back to the mobile device or other computer device, but rather simply stores, processes and/or uses the data.

In an alternative embodiment, the barcode or other type of ID or scannable image is encoded data. As previously described with reference to FIG. 2, the image can be scanned/captured by the camera 25 of a mobile device 24 using suitable reader software. However, rather than extracting an access address, the mobile device software decodes the data and displays it on the screen of the mobile device for review by the user.

The invention could be embodied in the medical apparatus itself, or the method by which it operates, the computer system or the method by which it operates, the software run on the mobile device or the manner in which it operates or the method of transferring data using the apparatus described or any other combinations thereof.

The invention claimed is:

1. A method of providing access to data from a medical apparatus for review and storage on a computer system, wherein the medical apparatus generates a barcode, the barcode encoding a URL comprising an access address for a computer system and patient-specific data from the medical apparatus as a sub-path appended to the access address, wherein the sub path was updated based on the use of the medical apparatus by the patient over a period of time, wherein a mobile telecommunications device extracts the URL from the barcode, wherein the mobile telecommunications device sends a request for access to the computer system, the request comprising the URL, the method comprising:

executed at the computer system, receiving the request for access from the mobile telecommunication device, in a pre-processor of the computer system, intercepting the request comprising the URL rather than using the sub path of the URL to return a static web page to the mobile telecommunications device;

in the pre-processor of the computer system, extracting the sub path from the URL;

in the pre-processor of the computer system, extracting the patient-specific data from the sub path;

in the pre-processor of the computer system, storing the extracted patient-specific data on a database of the computer system;

in the pre-processor of the computer system, dynamically composing a web page from the patient-specific extracted data; and returning the dynamically composed web page to the mobile telecommunications device as though the mobile telecommunications device has accessed a static web page.

2. The method according to claim 1, wherein the mobile telecommunication device is configured to capture an image of the barcode from a display of the medical apparatus and decode the barcode to extract the URL comprising the access address and the sub path.

3. The method according to claim 1, wherein a controller of the medical apparatus is configured to generate the barcode and display the barcode on the medical apparatus.

4. The method according to claim 3, wherein the controller is configured to dynamically generate the barcode each time patient-specific data is generated.

5. The method according to claim 3, wherein the controller is configured to dynamically generate the barcode each time patient-specific data is to be transferred.

6. The method according to claim 1, wherein the barcode is a 2D barcode or a 1D barcode.

7. The method according to claim 1, wherein the patient-specific data comprises at least one of the following:
runtime data;
usage time data;
AHI data;
leak data;
compliance data;
usage data; and
efficacy data.

8. The method according to claim 1, wherein the medical apparatus comprises a breathing assistance apparatus.

9. The method according to claim 1, wherein the medical apparatus comprises a PAP apparatus.

10. The method according to claim 1, wherein the medical apparatus comprises a flow therapy apparatus.

11. The method according to claim 1, wherein the mobile telecommunication device is the mobile telecommunication device of the patient.

12. The method according to claim 1, wherein the web page displaying the extracted patient-specific data comprises a graph or a table.

13. The method according to claim 1, wherein the barcode is a QR code.

14. The method according to claim 1, further comprising dynamically generating instructions for rending the web page and returning the instructions for rendering the web page to the mobile telecommunications device or other device where the web page is rendered.

15. A method of providing access to data from a medical apparatus for review and storage on a computer system, wherein the medical apparatus generates a barcode, the barcode encoding a URL comprising an access address for a computer system and captured patient-specific data from the medical apparatus as a sub-path appended to the access address, wherein the sub path was updated based on the use of the medical apparatus by the patient over a period of time, wherein a mobile telecommunications device extracts the URL from the barcode, wherein the mobile telecommunications device sends a request for access to the computer system, the request comprising the URL, the method executed at the computer system comprising:
- receiving the request for access from the mobile telecommunications device;
- intercepting the request comprising the URL rather than using the sub path of the URL to return a static web page to the mobile telecommunications device;
- extracting the sub path from the URL;
- extracting the captured patient-specific data from the sub path;
- storing the extracted captured patient-specific data on a database of the computer system;
- dynamically composing a web page from the captured patient-specific extracted data; and
- returning the dynamically composed web page to the mobile telecommunications device as though the mobile telecommunications device has accessed a static web page.

16. The method according to claim 15, wherein the patient captures an image of the barcode from a display of the medical apparatus using the mobile telecommunications device prior to sending the request for access.

17. The method according to claim 16, wherein the medical apparatus generates a barcode that encodes the URL comprising the access address for the computer system and the captured patient-specific data as the sub path appended to the access address, the URL for use by the computer system to extract and store the captured patient-specific data; and wherein the medical apparatus displays the barcode on the display of the medical apparatus.

18. The method according to claim 17, wherein a controller is configured to dynamically generate the barcode each time captured patient-specific data is generated and/or is to be transferred.

19. The method according to claim 15, wherein the barcode is one of:
- a 2D barcode; and
- a 1D barcode.

20. The method according to claim 15, wherein the patient-specific data comprises at least one of the following:
- runtime data;
- usage time data;
- AHI data;
- leak data;
- compliance data;
- usage data; and
- efficacy data.

21. The method according to claim 15, wherein the medical apparatus is a breathing assistance apparatus.

22. The method according to claim 15, wherein the medical apparatus is a PAP apparatus or a flow therapy apparatus.

23. The method according to claim 15, wherein the barcode is a QR code.

24. The method according to claim 15, further comprising dynamically generating instructions for rending the web page and delivering the instructions for rendering the web page to the mobile telecommunications device or other device where the web page is rendered.

* * * * *

UNITED STATES PATENT AND TRADEMARK OFFICE
CERTIFICATE OF CORRECTION

Page 1 of 1

PATENT NO. : 10,971,266 B2
APPLICATION NO. : 14/646675
DATED : April 6, 2021
INVENTOR(S) : Benjamin Wilson Casse et al.

It is certified that error appears in the above-identified patent and that said Letters Patent is hereby corrected as shown below:

In the Specification

In Column 1, Line 14 (Approx.), delete "1. Field" and insert --Field--.

In Column 1, Line 23 (Approx.), delete "2. Description" and insert --Description--.

In Column 2, Line 30, delete "review" and insert --review.--.

In Column 3, Line 5, delete "review" and insert --review.--.

In Column 3, Line 24, delete "data" and insert --data.--.

In Column 5, Line 41, delete "regadin" and insert --reading--.

In Column 6, Line 15, delete "that that" and insert --that--.

In Column 7, Line 36 (Approx.), delete "12/345,6123456." and insert --123456123456.--.

In Column 8, Line 46 (Approx.), delete "0x01" and insert --0x01,--.

In Column 8, Line 48 (Approx.), delete "0x01k" and insert --0x01k,--.

In Column 8, Line 54 (Approx.), delete "0x14" and insert --0x14.--.

In the Claims

In Column 10, Claim 14, Line 55, delete "rending" and insert --rendering--.

In Column 12, Claim 24, Line 28, delete "rending" and insert --rendering--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*